United States Patent
Halmann et al.

(10) Patent No.: US 6,526,163 B1
(45) Date of Patent: Feb. 25, 2003

(54) ULTRASOUND SYSTEM WITH PARALLEL PROCESSING ARCHITECTURE

(75) Inventors: Menachem Halmann, Haifa (IL); Alexander Sokulin, Haifa (IL); Igor Katsman, Haifa (IL)

(73) Assignee: G.E. Diasonics Ltd. (IL)

( * ) Notice: Subject to any disclaimer, the term of this patent is extended or adjusted under 35 U.S.C. 154(b) by 0 days.

(21) Appl. No.: 09/197,995

(22) Filed: Nov. 23, 1998

(51) Int. Cl.$^7$ ................................................ G06K 9/00
(52) U.S. Cl. ........................ 382/128; 600/437; 600/443
(58) Field of Search ................................ 600/447, 456, 600/450, 458; 382/128, 129, 130, 131

(56) References Cited

U.S. PATENT DOCUMENTS

| | | | | |
|---|---|---|---|---|
| 4,509,526 A | * | 4/1985 | Barens et al. | 128/663 |
| 5,492,125 A | * | 2/1996 | Kim et al. | 600/443 |
| 5,528,302 A | | 6/1996 | Basoglu et al. | |
| 5,566,092 A | * | 10/1996 | Wang et al. | 702/185 |
| 5,573,001 A | * | 11/1996 | Petrofsky et al. | 128/661.01 |
| 5,600,574 A | * | 2/1997 | Reitan | 364/552 |
| 5,787,889 A | | 8/1998 | Edwards et al. | |
| 5,795,297 A | * | 8/1998 | Daigle | 128/600.07 |
| 5,860,931 A | * | 1/1999 | Chandler | 600/458 |
| 5,971,923 A | * | 10/1999 | Finger | 600/437 |

* cited by examiner

Primary Examiner—Bhavesh Mehta
Assistant Examiner—Abolfazl Tabatabai
(74) Attorney, Agent, or Firm—McAndrews, Held & Malloy, Ltd.; Peter J. Vogel; Michael A. Dellapenna

(57) ABSTRACT

An ultrasound system operating on a personal computer architecture comprising multiple processors controlled to operate in parallel to share ultrasound operations of the system. The multiple processors are controlled by software to share the operations associated with system setup, system control, scanning, data acquisition, beamforming, user interface service, signal processing, and scan conversion. The ultrasound system utilizes management software which divides operations associated with each function (such as signal processing and scan conversion) into parallel sub-operations or tasks. Each task is assigned by the operating system to a CPU. Any of the CPUs may be capable of performing any of the tasks. The CPUs operate in parallel to carry out the assigned tasks. Once all of the CPUs have completed the assigned tasks, the system may serially advance to the next ultrasound function.

48 Claims, 7 Drawing Sheets

ULTRASOUND SYSTEM WITH PARALLEL PROCESSING ARCHITECTURE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention generally relates to an ultrasound system and in particular to a personal computer (PC) based ultrasound system which utilizes multiple processors controlled to operate in parallel and to share processing responsibilities.

Ultrasound systems have been used for many years in the field of radiology by physicians to examine various areas of humans, such as the heart, arteries, organs, a fetus, and the like. Ultrasound systems typically include two primary sections, a front end and a back end. The front end section includes one or more ultrasound probes for scanning an area of interest within a patient. Conventional front end sections also include a beamformer hardware unit that enables transmission of ultrasound signals into the patient and acquires echo ultrasound signals therefrom. The front end section passes acquired echo signals to the back end section which performs signal processing upon the acquired echo signals. The back end section converts the processed echo signals to a format displayable on a CRT and displays the echo signals in a desired format, such as a graph, a 2-dimensional image, a 3-dimensional image, a black and white image of anatomic structure (B-mode image), a colorized image of moving fluid (color flow image) and the like.

In the past, the front and back end sections of ultrasound systems were constructed in a hardware intensive manner utilizing multiple hardware boards, each board of which performed predetermined dedicated operations. In past ultrasound systems, dedicated hardware boards were included to perform signal processing and separate dedicated hardware boards were provided to perform scan conversion, which is the task of translating the incoming data from its beam coordinate space, usually polar, to Cartesian coordinates space. In addition, past ultrasound systems required a separate central processor which controlled various dedicated hardware boards. The central processor did not perform signal processing or scan conversion. Instead, the central processor primarily performed system control operations, such as setup functions to configure the hardware boards when the system was turned on and management of the dedicated hardware boards throughout operation.

More recently, ultrasound systems have been proposed which utilize digital signal processors (DSP) to carry out signal processing and scan conversion. One or more DSPs are programmed to cooperate to perform signal processing. The DSPs dedicated to signal processing are housed on a set of one or more printed circuit boards. A separate set of DSPs housed on a separate set of printed circuit boards are programmed to perform scan conversion. However, even in systems using DSPs, each set of DSPs is dedicated to specific processing operations. Hence, a DSP configured to perform Doppler signal processing cannot perform scan conversion. In addition, ultrasound systems which utilized DSPs continue to require a separate central CPU to maintain system control.

More recently, in the early 1990s, the assignee of the present application introduced ultrasound systems based on the architecture of a personal computer (PC). These ultrasound systems were referred to as the ESI5000™ and Synergy™ systems. The ESI5000™ and Synergy™ systems included DSP boards for signal processing and a central processor for controlling overall operation of the ultrasound system. The central processor of the PC was used to carry out setup operations and to control the DSP boards. The central CPU in the Synergy™ system also performed scan conversion of Color Doppler images from polar coordinates to Cartesian coordinates. Also, the ESI5000™ and Synergy™ systems used separate beamformer hardware in the front end subsystem.

However, conventional ultrasound systems have experienced limitations. In particular, conventional ultrasound systems require the use of a central processor to carry out dedicated operations including system setup and overall control and separate beamformer hardware. Conventional systems also require at least some hardware boards and/or DSP boards to carry out dedicated signal processing such as spatial and temporal filtering, tissue motion filtering, Doppler processing and the like. The hardware boards and DSP boards programmed for signal processing are unable to do any other operations besides signal processing. During operation, the central CPU and beamformer may remain idle while a dedicated DSP performs signal processing in the conventional system. Likewise, the dedicated DSPs and beamformer remain idle throughout setup of the system, while the central CPU must perform all setup operations. Consequently, conventional systems have been unable to realize the full processing power of the beamformer, DSPs and central CPU.

A need remains for an improved ultrasound system to overcome the above-identified difficulties. It is an object of the present invention to meet this need.

SUMMARY OF THE INVENTION

It is an object of the preferred embodiment of the present invention to provide an ultrasound system which operates multiple CPUs in parallel to carry out all ultrasound functions, such as setup, system control, beamforming, signal processing and scan conversion.

It is a further object of the present invention to provide an ultrasound system which maximizes the use of available processors in the system.

It is a further object of the present invention to provide an ultrasound system which avoids the need to dedicate functions to any given processor.

It is a further object of the present invention to provide an ultrasound system which divides ultrasound operations into tasks assignable to separate processors.

It is yet another object of the present invention to provide an ultrasound system that recommends a preferred division of operations into tasks between processors to maximize use of processor time.

It is another object of the present invention to provide an ultrasound system that simplifies overall processing by serially stepping through the ultrasound operations.

It is another object of the present invention to provide an ultrasound system enables high priority functions, such as user-interface service, to interrupt sub-operations assigned to one or more CPUs, in order to enhance user response time.

It is another object of the present invention to provide a front end subsystem that does not require separate beamformer hardware.

It is a corollary object of the present invention to provide an ultrasound system that performs beamforming operations through software.

These and other objects of the present invention are provided by an ultrasound system operating on a personal computer architecture comprising multiple processors controlled to operate in parallel to share ultrasound functions of the system. The multiple processors are controlled by software to share the operations associated with system setup, system control, scanning, data acquisition, beamforming, user interface service, signal processing, and scan conversion. The ultrasound system utilizes management software which divides operations associated with each function (such as signal processing and scan conversion) into parallel sub-operations or tasks. Each task is assigned by the operating system to a unique CPU. Any of the CPUs may be capable of performing any of the tasks. The CPUs operate in parallel to carry out the assigned tasks. Once all of the CPUs have completed the assigned tasks, the system may serially advance to the next ultrasound function.

DETAILED DESCRIPTION OF THE PREFERRED EMBODIMENT

Figure 1:
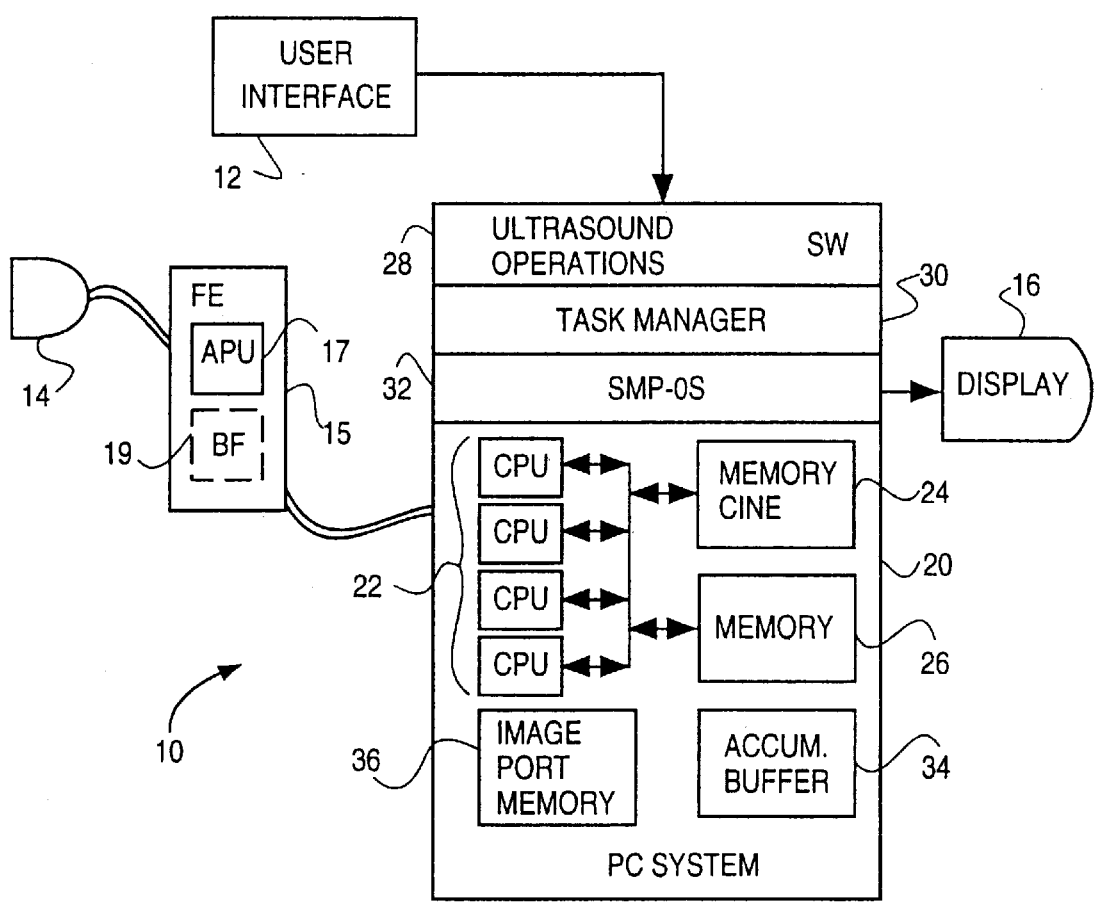
FIG. 1 illustrates an ultrasound system according to a preferred embodiment of the present invention including multiple CPUs controlled to perform parallel tasks.

FIG. 1 illustrates an ultrasound system 10 according to a preferred embodiment of the present invention. The ultrasound system 10 includes a user interface 12, a front end subsystem 15 having at least an acoustic power unit 17 to power the probe 14, a display 16 and a personal computer system 20. Optionally, the front end subsystem 15 may include a beamformer 19. Alternatively, the beamformer 19 may be removed and implemented in software as explained below. The user interface 12 permits users to interact with the ultrasound system 10, such as through the entry of patient information, selection of operating modes and selection of parameters. The probe 14 transmits and receives ultrasound signals to and from an area of interest in a patient. The transmitted ultrasound signals are focused and steered to an area of interest by beamformer 19 or a beamformer software module in the personal computer system 20 based upon the mode of operation and user selected parameters (as explained below in more detail). The probe 14 receives echo signals including echo signal intensity information, Doppler information and the like. The beamformer collects data points representative of the echo signals, forms data sets therefrom for each frame or scan of the area of interest and stores the data sets in image port memory 36 of the back end personal computer system 20 as image frames.

The back end personal computer (PC) system 20 includes multiple CPUs 22, CINE loop memory 24, memory 26, an accumulator buffer 34 and image port memory 36. The image port memory 36 may be omitted and memory 26 may be configured to include a segment dedicated to storage of data for beamforming operations. The PC system 20 further includes software modules to control the CPUs 22 as explained below in order to carry out all of the operations of an ultrasound system. The system software may be conceptually divided into three components, as depicted in FIG. 1 at reference numerals 28, 30 and 32. Reference numeral 28 depicts the ultrasound operations such as system set-up, interaction with the user interface, beamforming, signal processing, scan conversion and the like. The ultrasound operations software 28 may carry out the beamforming, signal processing and scan conversion operations and the like serially in order to ensure that the maximum number of CPUs 22 are available at each stage of operation for processing.

As explained below, one or more of the ultrasound operations may be divided into sub-operations or "tasks" to be performed in parallel by the multiple CPUs 22. The parallel tasks are managed by a task manager denoted as reference numeral 30. The task manager 30 manages the order of operation of the tasks. The PC system 20 may use a conventional Operating System (OS), such as Windows NT™ or any similar operating system that supports symmetrical multiprocessing (SMP), or similar multi-CPU capabilities. The ultrasound operations software 28 and task manager 30 therein of the preferred embodiment may be configured such that any of the ultrasound operations may be carried out by any or all of CPUs 22. No particular CPU is dedicated to perform system control, beamforming, signal processing, scan conversion and the like. By way of example, when the ultrasound operations software 28 carries out a system control function, the ultrasound operations software 28 divides the operations required by the system control function into multiple sub-operations or tasks. The divided system control tasks are managed by the task manager 30 and separately assigned by the SMP-OS 32 to corresponding CPUs 22. Each CPU 22 carries out an assigned one of the system control tasks. In some cases it may be desirable to bind a task to a specific CPU, and later un-bind the task. This improves the cache usage of the task. The decision to bind tasks to specific CPUs may be done in run-time. The task manager 30 may cooperate with the SMP-OS 32 to bind a task to a CPU.

In the preferred embodiment, the ultrasound operations software 28 may recommend a division of the tasks that the SMP-OS 32 assigns to the CPUs 22. The SMP-OS 32 assigns each task in a non-preferential manner to any of the CPUs 22. Preferably, the SMP-OS 32 evenly divides the tasks between the CPUs 22. Alternatively, the ultrasound operations software 28 may assign a higher priority to certain operations, such as service of the user interface. The operations assigned higher priorities may interrupt a task or tasks of lower priority that is currently being carried out by one or more of the CPUs 22. For example, if all four CPUs 22 in the preferred embodiment of FIG. 1 are performing scan conversion operations when a user interface operation must be performed, the ultrasound operations software 28 may direct one or more of the CPUs 22 to interrupt the scan conversion processing and carry out the user interface request thereby avoiding delay in responding to user entries. While the ultrasound operations software 28 may recommend a task distribution among the CPUs 22, if one CPU finishes before another, the SMP 38 may redistribute the remaining uncompleted tasks in order to utilize the full capacity of the parallel processors. While four CPUs 22 are illustrated, any number of CPUs may be used. The ultrasound operations software 28 is configured to divide ultrasound operations into a number of tasks based on the number of CPUs. Therefore, if two CPUs are used, each ultrasound operation may be divided into two tasks. When dividing a task between several CPUs, the following aspects are taken into consideration: better cache memory utilization. minimal overhead of task-switch management, and balanced loading between CPUs.

Figure 2:
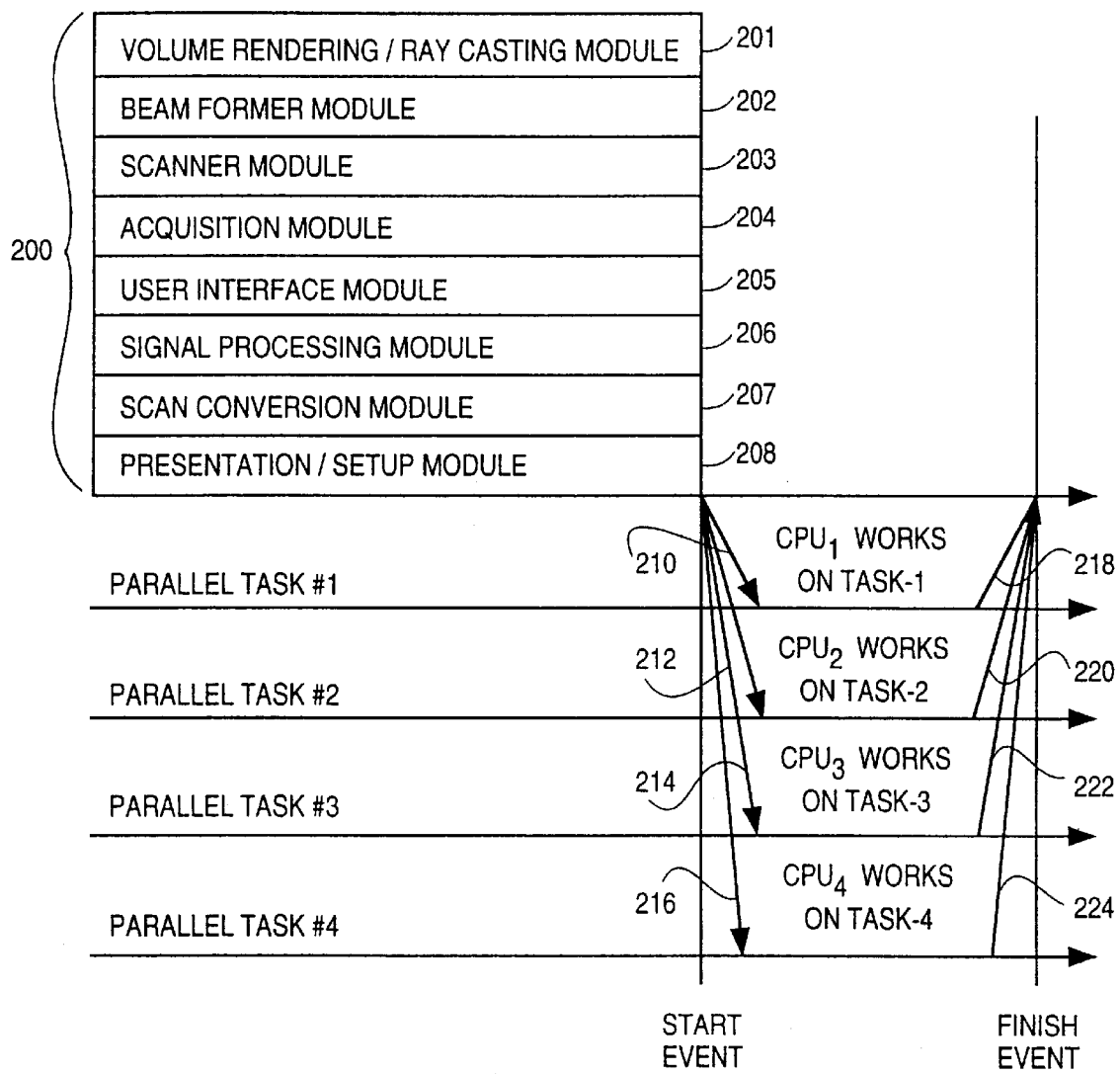
FIG. 2 illustrates an exemplary process flow between ultrasound operations and multiple CPUs according to the preferred embodiment of the present invention.

FIG. 2 illustrates the general processing flow between the ultrasound operations software 28 and the implementation by the CPUs 22 of parallel tasks. Block 200 generally sets forth the exemplary modules included within the ultrasound operations software 28, including a volume rendering/raycasting module 201, a beamformer module 202, a scanner module 203, an acquisition module 204, a user interface module 205, a signal processing module 206, a scan conversion module 207 and a presentation module 208. Each of the modules 201–208 within the block 200 represents a self contained software module which carries out all desired operations and responsibilities as described below, including division of the corresponding ultrasound operation into parallel sub-operations or tasks to be carried by the CPUs 22.

The volume rendering/raycasting module 201 constructs a 3-dimensional volume of a series of 2-dimensional images. The module 201 then performs known volume rendering and/or raycasting techniques to produce an image for display. The 3D volume may contain B-mode images, color Doppler images or both.

The presentation module 208 processes and displays the ultrasound information, such as images, traces and the like. The presentation module 208 may also be responsible for handling CINE loops, management of ultrasound databases, management of patient information and interaction with any measurement applications. The presentation module 208 may also include any management or control operations necessary for the system, including management of processes for incoming ultrasound data, such as tissue, CFM, Doppler, traces and the like.

The scanner module 203 handles user interface events received from the user interface module, determines the mode of a scan to be taken and passes scan parameters based upon the scan mode to the acquisition module 204. The acquisition module 204 handles requests for scan parameter changes, implements scan parameter changes, and translates scan parameters as required by the hardware within the probe 14. The acquisition module 204 carries out scan sequences in a desired manner, and transfers hardware events (e.g., overpower, probe disconnect, and the like). The acquisition module 204 also receives ultrasound data sets that have been collected and formed by the beamformer module 202 and relays the data sets to the presentation module.

The user interface module 205 provides menus for the user, displays scan parameters, and monitors the front panel and the trackball. The user interface module 205 also is responsible for the display of images, the set-up of menus, and the delegation of menu events, front panel events and trackball events to the scanner module. The user interface 205 handles trackball assignments, sets up a front panel dialog (such as for software debug), and displays scan parameters and ultrasound images.

The signal processing module 206 performs all signal processing of the data sets based upon the mode of operation. Signal processing may include vector processing, such as Doppler, CFM, image processing and the like. The scan converter module 207 converts incoming data from the polar coordinate system to the Cartesian coordinate system. The foregoing modules 201–208 may divide the operations associated with each module into tasks which are then assigned by the SMP-OS 32 to corresponding CPUs 22.

Optionally, the ultrasound operations associated with each module may be assigned an order of priority. Thus, while the ultrasound operations generally may follow a serial flow of operation, the serial flow may be interrupted intermittently with operations having a higher priority. For example, the operations may generally sequence between beamforming, acquisition, signal processing and scan conversion. However, a scan conversion operation may be interrupted by a user interface service request or a beamformer operation (such as to transmit a new ultrasound signal or form a data set based on echo signals).

Returning to the illustration of FIG. 2, in the preferred embodiment, the modules 201–208 divide corresponding operations into four tasks which are assigned to the four CPUs 22 in the PC system 20. In FIG. 2, arrows 210–216 reflect the assignment of sub-operations or tasks from one of modules 201–208 to each of the four CPUs. The arrows 210–214 may also be referred to as tasks. The SMP-OS 32 assigns each task 210–214 to a CPU. Upon receipt by each CPU 22 of an associated task, the CPU 22 carries out the associated task until complete or interrupted by a higher priority task. In the example of FIG. 2, the first through fourth CPUs carry out parallel tasks #1–4. When each CPU completes its associated task, it returns an event to the ultrasound operations software 28 informing the ultrasound operations software 28 that the requested operation(s) have been completed. The return events are pictorially depicted by arrows 218–224 in FIG. 2. Once the ultrasound operations software 28 receives the completion events 218–224 from all four CPUs, the ultrasound operations software 28 sequentially advances processing.

Optionally, the division of operations by the modules 201–208 into parallel tasks 30 may be considered by the operating system to be a recommended distribution of operations which the operating system need not necessarily follow. Instead, the operating system may override the recommended task distribution and reassign tasks between the multiple CPUs in a more efficient manner, such as when one CPU is experiencing difficulty or an excessively heavy processing load.

By way of example only, the signal processing module 206 may divide Doppler processing into four tasks, wherein each Color Doppler processing task performs Doppler processing upon one-fourth of a sector scan (e.g., one quadrant). However, a first of the four quadrants of the sector scan may have little or no Doppler information, while a second quadrant may have a large amount of Doppler information. Thus, the CPU assigned to perform Doppler processing for the first quadrant will finish quickly and become idle, while the CPU assigned to the second quadrant will not. When the CPU for the first quadrant completes processing, the SMP- OS 32 may re-divide and re-assign to the idle CPU all or a part of the remaining Doppler processing for the second or remaining quadrants. Similarly, when one CPU has not completed its assigned sub-tasks, but the other three CPUs have completed their assigned sub-tasks, the one remaining sub-task may be re-divided between all of the CPUs so that the full task will finish faster. By affording the option of overriding the recommended task distribution, the system prevents the ultrasound operations software 28 from delaying or "hanging up" while waiting on one particular CPU.

Optionally, the modules 201–208 may divide operations into sub-tasks on a frame by frame basis. For example, the signal processing module 206 and scan converter module 207 may direct a first CPU to perform all signal processing and scan conversion associated with a first frame received from the front end 15. A second CPU may perform all signal processing and scan conversion associated with a second frame. In a frame-by-frame implementation, each CPU may perform an entire operation associated with a frame, while new frames are assigned to new CPUs as the CPUs become available.

Alternatively, the multiple CPUs may be managed such that a subset of the CPUs is designated as "preferred processors", whereby the system attempts to utilize the preferred processors for certain functions. By way of example, the system may attempt to utilize the preferred processors for all signal processing, while a separate subset of processors preferably performs control operations and the like. This alternative configuration may be desirable when the processors within the system are not of equal processing capability. In the preferred embodiment, it is assumed that the CPUs are of equal processing capability and thus may equally share in all ultrasound operations.

Figure 5:
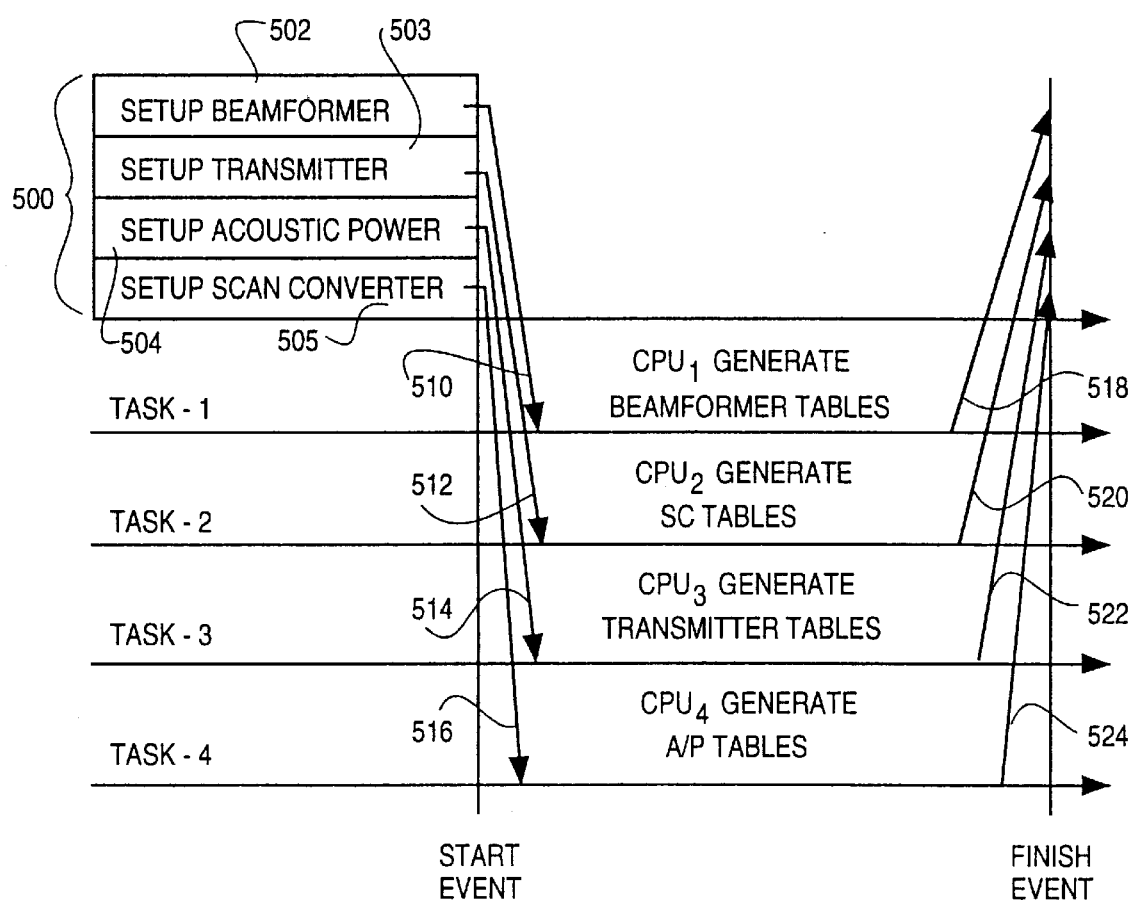
FIG. 5 illustrates an exemplary processing flow between the presentation module and multiple CPUs according to the preferred embodiment of the present invention.

FIG. 5 illustrates an exemplary process flow between the ultrasound operations software 28 and the CPUs 22 during setup operations. Block 500 generally denotes the setup operations which, by way of example only, may include at least four setup operations. The setup operations are carried out when the system 10 is initially started. The setup operations may include the generation of tables to be used by the system 10 during ultrasound image scanning and image display. Block 500 depicts four setup tasks, namely setup beamformer task 502, transmitter task 503, acoustic power task 504 and scan converter task 505. In the example of FIG. 5, each of the setup tasks 502–505 corresponds to a separate software function performed during implementation of the presentation module 208. The CPUs 22 are each assigned by the SMP-OS 32 to a unique setup task 502–505. The tasks 502–505 are passed to corresponding CPUs 22 via instructions depicted by arrows 510–516. The first CPU carries out a beamformer setup task 502 which includes the generation of tables to be used by the beamformer module 202 during operation. The beamformer tables generated by the first CPU are based upon the selected mode of operation. The fourth CPU generates the scan converter tables necessary to convert scanned data from the polar coordinate system to the Cartesian coordinate system. The tables generated by the fourth CPU are dependent upon the selected mode of operation. The second and third CPUs similarly generate tables to be used by the transmitter and for the acoustic power, respectively. Dividing the setup operations among all of the multiple CPUs greatly reduces the setup time and enhances the system performance.

Figure 3:
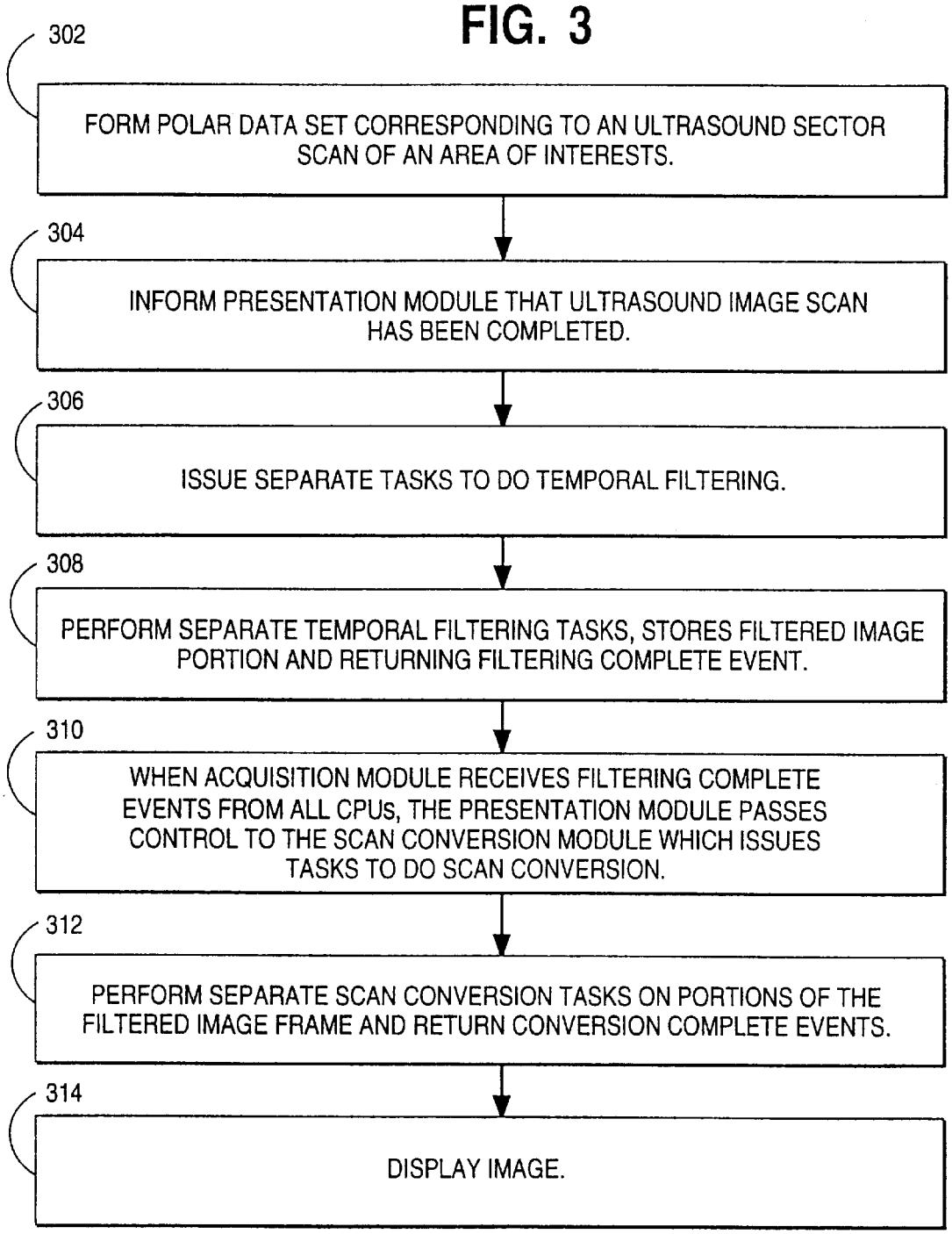
FIG. 3 illustrates a processing sequence followed by the preferred embodiment of the present invention to carry out signal processing and scan conversion for a B-mode image.
Figure 4:
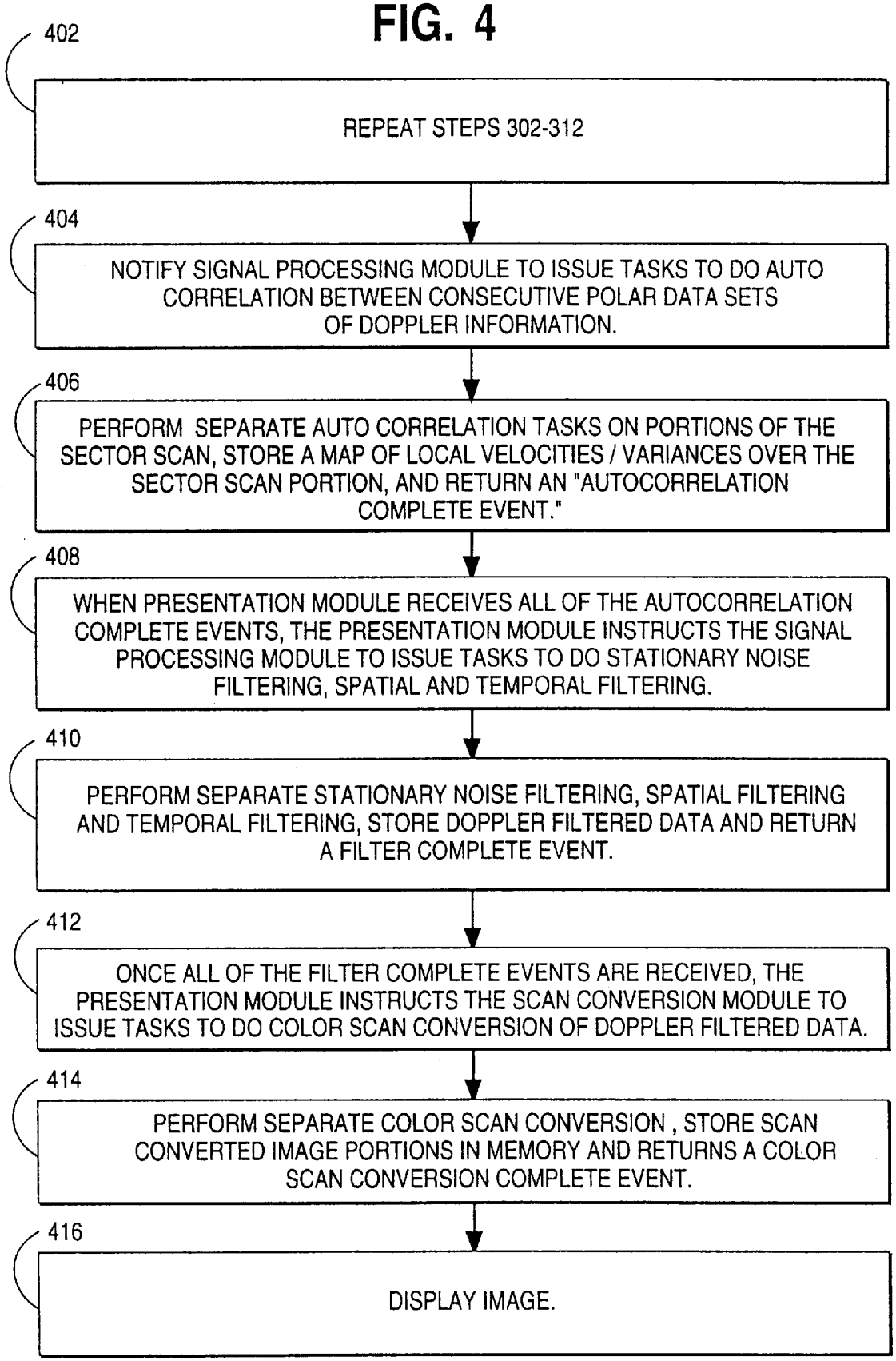
FIG. 4 illustrates the processing sequence carried out by the preferred embodiment of the present invention to effect signal processing and scan conversion of a color flow image.

FIGS. 3 and 4 illustrate an exemplary processing sequence whereby the multiple CPUs are controlled to perform B-mode image acquisition and display, and color-flow image acquisition and display. Beginning with FIG. 3, at step 302, the beamformer module 202 forms a set of polar data values corresponding to an ultrasound sector scan or image frame of an area of interest. The polar data set is formed by collecting digital representations of echo signals detected by the probe 14 from one or more firings of ultrasound signals focused at an area of interest. The beamformer module 202 collects the digitized echo signals and performs beamforming functions upon the digitized echo signals to form the polar data set. Alternatively, the beamformer module 202 may be omitted and a conventional beamformer front-end hardware unit substituted therefore. The conventional beamformer front end may be located between the probe 14 and the PC system 10. When the conventional beamformer front end is utilized, the acquisition module 204 carries out interaction with the front end and the beamformer.

Returning to FIG. 3, once a polar data set is collected in step 302, the beamformer module 202 stores the polar data set in the image port memory 36 and notifies the presentation module 208 that an ultrasound image scan has been completed (step 304). The presentation module 208 directs the acquisition module 204 to store the polar data set in CINE memory 24. In the preferred embodiment, the operating system treats each of the multiple CPUs 22 as any other resource within the system, such as memory, the printer, etc. The operating system passes each task to the next available CPU 22 which, in turn, carries out the task. Following step 304, the acquisition module 204 issues a set of N tasks (e.g., to conduct temporal filtering upon the polar data set) (step 306). Each temporal filtering task is passed by the operating system to the available CPUs 22. By way of example, if the system utilizes four CPUs, the acquisition module 204 at step 304 may issue four temporally filtering tasks to begin temporal filtering four discrete quadrants of the image frame. Each temporal filtering task is assigned to a separate CPU. At step 308, each CPU that receives a task separately performs temporal filtering upon the polar data for an associated quadrant of an image frame.

Temporal filtering such as frame averaging between consecutive image frames is performed to improve the temporal continuity of the subsequently displayed image. Optionally, the CPUs may carry out temporal filtering through the use of infinite impulse response (IIR) filters. When each CPU completes temporal filtering of the polar data set of the image quadrant assigned to that CPU, the CPU stores a filtered data set for the corresponding image quadrant in memory. The CPU then returns a "filtering complete event" to inform the acquisition module 204 that the temporal filtering operation has been completed for the corresponding quadrant of the polar data set. The acquisition module 204 waits until every task returns a "filtering complete event" before continuing to the next serial operation. When all of the filtering complete events are received, at step 310, the acquisition module 204 returns control to the presentation module 208 which directs the scan conversion module 207 to issue tasks to perform scan conversion. The scan conversion module 207 includes multiple tasks that divide the filtered image frame into segments. The operating system assigns each scan conversion task to a different CPU in order that multiple CPUs within the system may share the scan conversion operation and operate in parallel. The multiple CPUs carry out the scan conversion operation in parallel by separately operating upon assigned segments of the filtered image frame. The CPUs operate in parallel to convert the polar coordinate data set to a Cartesian coordinate data set. The scan conversion function performed by each task may be carried out in a number of known manners, such as through interpolation and the like. Each scan conversion task instructs the corresponding CPU to store the related portion of the scan converted image in a predetermined segment of memory. Once the scan converted image portions are stored in memory, each scan conversion task returns a "scan conversion complete event" to the presentation module 208 informing the presentation module 208 that the corresponding scan conversion task has completed conversion of its assigned portion of the image frame (step 312). Once the presentation module 208 receives "scan conversion complete events" from all of the tasks, the presentation module 208 continues processing, such as by displaying the image (step 314).

FIG. 4 illustrates the processing sequence to be carried out during display of a colorflow image based on Doppler information. Beginning at step 400, the steps 302–312 discussed above in connection with FIG. 3 are repeated. At step 302, a polar data set is collected corresponding to an ultrasound sector scan of an area of interest. The polar data sets include echo intensity information (B-mode information) and Doppler signal information (e.g., frequency and/or phase shifts between successive echo signals). The beamformer module 202 collects Doppler information and a complex signal containing I and Q information (e.g. in-line and quadrature phase information). The Doppler information is processed as explained below in connection with steps 402–412, while the echo intensity (B-mode) information is processed as described above in connection with steps 304–312.

By way of example only, the presentation module 208 may first carry out the temporal filtering and 2D B-mode scan conversion of the echo intensity information from the polar data set. Once the B-mode information is scan converted, the presentation module 208 notifies (at step 402) the signal processing module 206 which issues tasks to begin auto-correlation between consecutive polar data sets of Doppler information. The signal processing module 206 issues tasks that divide the Doppler information into segments corresponding to quadrants of the image frame. The number of tasks is based upon the number of CPUs within the system in order that each CPU may process Doppler information from a unique, but preferably equal share, of the image frame. Thus in a four processor system, the signal processing module 206 may divide the Doppler information into four segments which are distributed among four signal processing tasks.

The operating system assigns each signal processing task to a separate CPU which performs auto-correlation upon an associated portion of the image frame. The tasks may utilize conventional auto-correlation techniques which provide velocities and/or variances of the echo information. Once each CPU completes auto-correlation of its associated portion of the image frame, the CPU stores in memory a map of local velocities and/or variances of the echo information over the associated image frame portion. Next, each CPU returns an "auto-correlation complete event" to the presentation module 208. At step 406, once the presentation module 208 receives all of the auto-corrolation complete events, the presentation module 208 next notifies each signal processing module to issue tasks that perform filtering upon associated portions of the image frame (step 408). Filtering may include stationary noise filtering, spatial filtering, temporal filtering and the like (step 410). Stationary noise filtering may be utilized to remove Doppler information associated with moving tissue. Several stationary noise filters exist, such as wall filters and the like. Spatial filtering may involve averaging of velocity and/or variance information from neighboring data points within the image frame portion. Temporal filtering may involve averaging of velocity and/or variance information for associate data points within consecutive image frames portions (step 408).

Once each CPU completes filtering, it stores in memory Doppler filtered data for a corresponding portion of the image frame and returns a "filter complete event" to the presentation module 208 (step 410). At step 412, when the presentation module 208 receives all of the filter complete events from the CPUs, the presentation module 208 instructs the scan conversion module 207 to issue tasks to perform color scan conversion of the Doppler filtered data. The operating system assigns each scan conversion task to a CPU which performs color scan conversion upon the associated segment of Doppler filtered data. The CPUs then store the scan converted Doppler filtered data in memory and return a color scan conversion complete event to the presentation module 208. Once the presentation module 208 receives all of the color scan conversion complete events, the presentation module 208 displays the resulting color flow image (step 416). The foregoing process is continuously repeated for consecutive image frames.

The ultrasound operations software 28 may be configured, whereby processing sequences call upon tasks in multiple modules 202–208. For instance the processing sequence for displaying a B-mode image may call upon tasks in the beamformer, acquisition and scan conversion modules 202, 204 and 207, respectively. Each processing sequence may also be referred to as a "thread" or function. Exemplary threads are discussed below in more detail.

By way of example only, when performing 2-dimensional tissue scanning, two distinct processing functions may be performed, acquisition and imaging. The acquisition function involves acquiring data in the CINE memory and performing temporal filtering between frames, such as with an infinite impulse response (IIR) filter or similar filter that combines a new acoustic frame with an accumulator buffer. Temporal filtering may be done for each acoustic frame. The imaging function is performed on the output of the temporal filter and may involve geometric conversion and filtering. Imaging may be performed for every acoustic frame, up to a maximum display rate.

The acquisition tasks may have above-normal priority and may be triggered by a "New Frame Event" which is issued by the PC system 10 when a new image frame is received by the beamformer module 202. The acquisition tasks place the new frame in a correct position in the CINE-loop memory 24, and perform temporal filtering upon the new frame. The acquisition tasks store the filtered image frame to an accumulator buffer 34 in the PC system 10, and trigger a 2-dimensional imaging event, thereby directing the PC system 10 to begin 2-D imaging.

The ultrasound operations software 28 also includes "Periodic Threads" to periodically test the system, "User Event Threads" to handle user interface events, update system parameters and provide feedback to the user, and "SysUpdate Threads" which stop acquisition, update the front-end and back-end, and restart acquisition. The Periodic Thread and User Event Thread may have high priorities, while the SysUpdate Thread may have a normal priority. The presentation module 208 may include two primary groups of ultrasound functions, referred to as "threads", performed in real time. The real time threads generally may be divided into data generation threads and imaging threads. The data generation and imaging threads initiate in the presentation module 208, but interact with, and call upon, tasks in the other modules 202–207 to carry out each ultrasound function.

For example, the data generation threads (functions) may include an acquisition thread, a simulator thread and a CINE thread. The acquisition thread is part of the acquisition module 204. The simulator thread simulates acquisition when no actual data is acquired. The CINE Thread simulates data acquisition using data and time stamps stored in CINE-loop memory 26. The data generation threads trigger an appropriate thread from the imaging thread group based on the current mode of operation. The imaging threads include a "BCThread", "DopThread", and "MThread". The BCThread may carry out 2-D and CFM vector processing, scan conversion and display. The DopThread may carry out Doppler vector processing, audio playback and Doppler spectrum display. The MThread may carry out M-mode vector processing, scan conversion and display.

When the acquisition tasks trigger 2-D imaging, a "BCThread" (B-mode task) obtains the new image frame from the accumulator buffer 34, and directs the scan conversion module 207 to scan convert the new image frame. Next, the BCThread displays the new image frame.

When performing color flow imaging, the acquisition task triggers a "DopThread" (Doppler signal processing task) which obtains the new image frame from the accumulator buffer 34, and directs the signal processing module 206 to perform Doppler processing on the image frame. The DopThread then passes the processed image to the scan conversion module 207. Similarly, when performing M-mode scanning, an "MThread" is triggered by the acquisition task and performs M-mode processing, scan conversion and image display. The BCThread, DopThread and MThread may have low priorities.

The acquisition module 204 receives a "New Frame Interrupt" once the beamformer module 202 collects and forms a new image frame. The acquisition module 204 sends a "New Frame Event" to the acquisition thread which stores the data in CINE-loop memory and dispatches the New Frame Event to the appropriate imaging thread. The beamformer module 202 issues the New Event Interrupt after the new frame/packet is stored in image port memory 36. The acquisition thread may issue a direct memory access (DMA) to copy the frame from the image port memory 36 to the correct address in CINE-loop memory 26 as determined by the presentation module 208. The number of vectors per frame/packet may be programmable.

Figure 6:
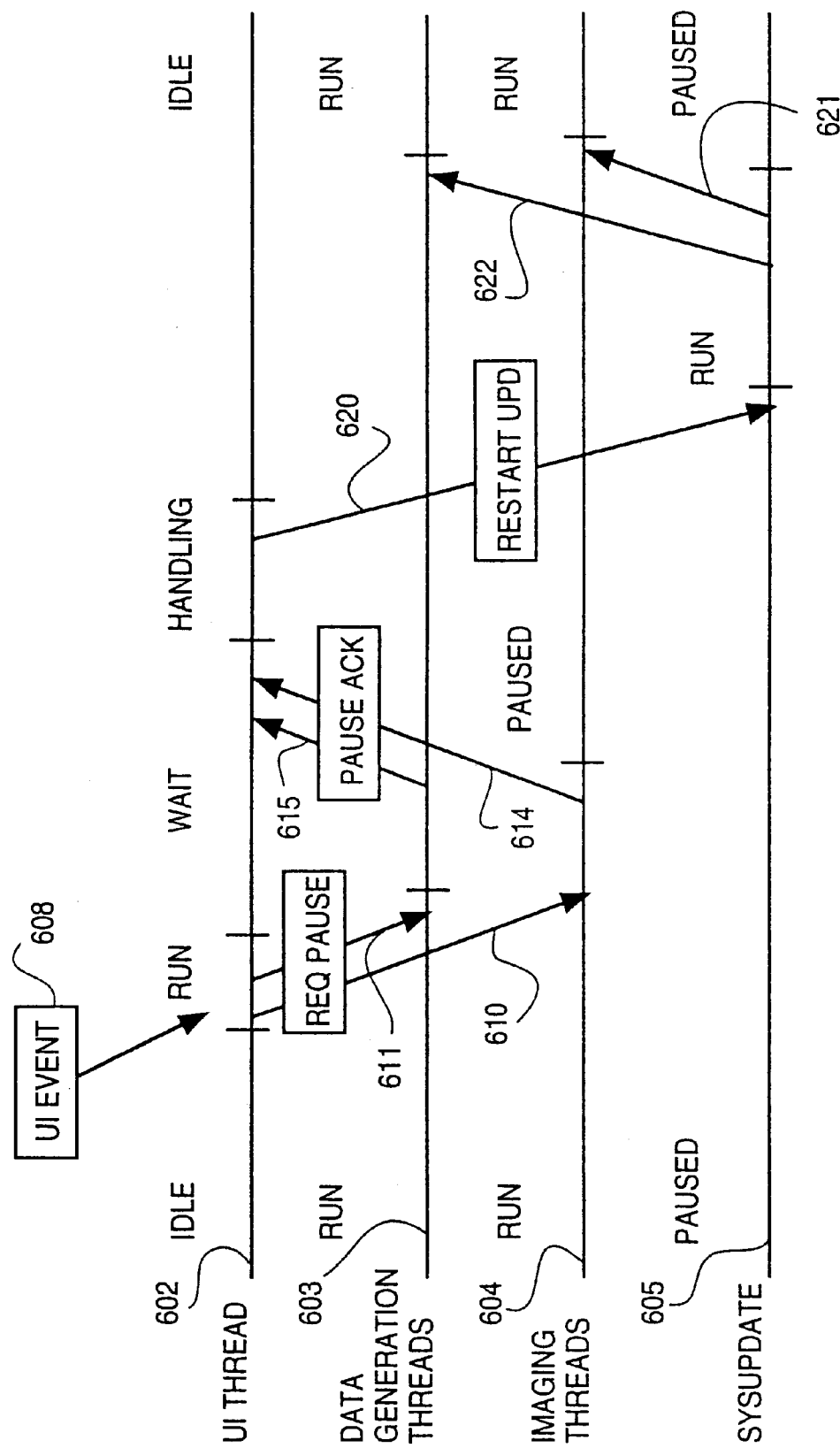
FIG. 6 illustrates an exemplary processing sequence carried out during a user interface event according to a preferred embodiment of the present invention.

FIG. 6 illustrates an example of the processing sequence for handling a user interface event. FIG. 6 illustrates four separate threads operating in parallel, namely a user interface (UI) thread 602, a data generation thread 603, an imaging thread 604 and a system update (SysUpdate) thread 605. Initially, the UI thread 602 and SysUpdate thread 605 are idle, while the data generation and imaging threads 603 and 604 are running. The user interface module 205 receives a UI event 608 and activates the UI thread 602. The UI thread 602 stops the front end subsystem 15 and the beamformer module 202 and instructs the tasks in threads 603 and 604 to pause (indicated at instructions 610 and 611 in FIG. 6). The threads 603 and 604 enter a pause state and return pause acknowledge events 614 and 615. The UI thread 602 updates the system parameters based on the UI event 608 and initiates the SysUpdate thread 605 (at instruction 620 in FIG. 6). The SysUpdate thread 605 updates the system and instructs the threads 603 and 604 to resume running at instructions 621 and 622.

CPUs may be busy 100% of the time during normal scanning. Generally, the ultrasound operations software 28 may be configured to handle every acoustic frame such that the frame is stored properly in the CINE-loop memory and the frame is temporally processed. Any remaining CPU power may be used for scan-conversion and image display. The ultrasound operations software 28 also provide time slots for infrequent system management task.

Figure 7:
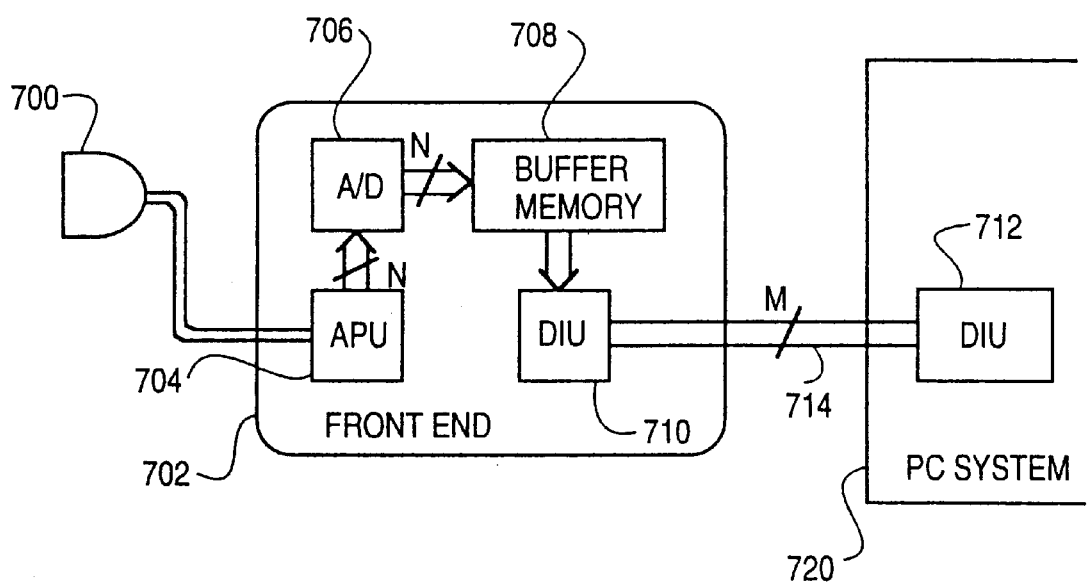
FIG. 7 illustrates a front end subsystem according to an alternative embodiment of the present invention.

FIG. 7 illustrates an alternative embodiment for the front end subsystem 702. The front end subsystem 702 is attached to a probe 700 and to the back end PC system 720. The front end subsystem 702 constitutes a hybrid type system whereby a portion of the beamforming operations have been moved to the PC system 720 into a software beamforming module resembling module 202. The front end subsystem 702 includes an acoustic power unit 704 to provide power to the probe 700 during ultrasound scanning. The probe 700 receives echo signals which are passed through the acoustic power unit 704 to A/D converter 706 which digitizes the incoming analog representations of the echo signals. The A/D converters 706 includes a plurality of parallel channels N corresponding to the number of transducer elements within the probe 700. Incoming N analog echo signals are digitized and output as an equal plurality of parallel digital signals N. The output N digital signals from the A/D converter 706 are passed to a temporary buffer memory 708 to store the digitized echo signals temporarily. The digitized echo signals are passed from the buffer memory 708 to a digital interface link comprising a digital interface unit 710, a digital interface connector 714 and a digital interface unit 712 in the PC system 720. The digital interface link 710–714 affords an extremely fast link for passing the digitized echo signals to the PC system 720 for processing for the beamforming software module. The PC system 720 stores in its standard memory the digitized echo signals received through the digital interface unit 712 for subsequent beamforming processing.

The beamforming tasks are divided between the available CPUs as explained above. For example, each CPU may perform beamforming operations upon a subset of channels associated with a subset of transducer elements (also referred to as sub-apertures). The beamforming software module 202 performs beamforming operations including summing channels together with an appropriate delay between channels to achieve effective acoustical focusing. In addition, since the digitized echo signals are stored in the PCs memory, the beamforming software module 202 may perform beamforming upon information received from multiple scans (also referred to as synthetic aperture imaging). Alternatively, the digital interface unit 702 and buffer memory 708 may be controlled within the front end subsystem 702 to perform grouping of subsets of the digitized echo signals associated with neighboring transducer elements to produce subsets of digital information associated with sub-apertures. The resulting subsets of data may then be passed over the digital interface link 710–712 to the PC system 720, thereby reducing the amount of processing required of the PC system 720 associated with beamforming, without requiring the complexity in the front end subsystem 702 of an entirely separate beamformer. In this alternative configuration, the beamforming module 702 in the PC system 720 combines the subsets of data for sub-apertures into data sets associated with beams, thereby reducing the software complexity required while retaining the flexibility afforded by implementing the majority of the beamforming operations and software.

Implementing all or a portion of the beamforming operations in software within the PC system 720 allows several software beamforming operations to be carried out upon a single data set or associated with a set of sub-apertures (referred to as multi-line acquisition).

Although the present invention has been described with reference to specific embodiments, those of skill in the art will recognize that changes may be made thereto without departing from the scope and spirit of the invention as set forth in the appended claims.

What is claimed is:

1. A method of processing ultrasound information in a medical diagnostic imaging ultrasound system having multiple CPUs configured to perform parallel ultrasound operations, said method comprising:

collecting data sets representative of patient ultrasound scans of an area of interest of a patient;

dividing a signal processing operation into parallel signal processing tasks;

instructing multiple CPUs to perform, in parallel, signal processing tasks upon said data sets to form processed data sets, said multiple CPUs processing said signal processing tasks simultaneously and in parallel;

reassigning uncompleted signal processing tasks among said multiple CPUs based upon completion of at least one of said signal processing tasks; and presenting ultrasound information to a user representative of said ultrasound scans based on said processed data sets.

2. The method of claim 1, further comprising:

dividing a scan conversion operation into parallel scan conversion tasks; and instructing said multiple CPUs to perform, in parallel, scan conversion tasks upon said processed data sets.

3. The method of claim 1, further comprising instructing the multiple CPUs to perform said scan conversion tasks simultaneously and in parallel with said parallel signal processing tasks.

4. The method of claim 1, further comprising:

instructing the multiple CPUs to perform system control tasks simultaneously and in parallel with said signal processing tasks.

5. The method of claim 1, further comprising:

interrupting operation of at least one of the multiple CPUs while performing associated parallel signal processing tasks; and instructing an interrupted CPU to perform a user-interface operation, while uninterrupted CPUs continue to perform associated parallel signal processing tasks.

6. The method of claim 1, further comprising:

determining when a first CPU completes an associated first parallel signal processing task and at least a second CPU has not completed an associated second parallel signal processing task; and instructing the first CPU to complete the second parallel signal processing task and the second CPU to cease performing the second parallel signal processing task.

7. The method of claim 1, wherein said dividing step includes dividing a data set associated with a single image frame into data subsets based on a number of CPUs, wherein each data subset corresponds to a unique segment of the image frame and wherein said instructing step instructs each CPU to perform a parallel signal processing task upon a corresponding data subset of a single image frame.

8. The method of claim 1, wherein the dividing step divides the data set into at least two data subsets corresponding to at least two unique quadrants of an ultrasound scan and having substantially equal complexity.

9. The method of claim 1, wherein the collecting step collects at least first and second data sets corresponding to first and second image frames of an area of interest, respectively; and the instructing step instructs first and second CPUs to perform all signal processing upon corresponding first and second data sets, respectively.

10. The method of claim 1, wherein each parallel signal processing task includes all signal processing for a data set associated with an image frame of the area of interest.

11. The method of claim 1, wherein the instructing step assigns each CPU to a data set associated with a complete image frame of the area of interest, the multiple CPUs being assigned to successive image frames.

12. The method of claim 1, wherein the instructing step directs at least two CPUs to perform parallel signal processing tasks upon at least two unique data subsets representing unique segments of a single ultrasound scan.

13. The method of claim 1, further comprising:

waiting until completion of said signal processing operation by all of the multiple CPUs before beginning another ultrasound operation.

14. The method of claim 1, further comprising:

dividing setup operations into parallel setup tasks, at least first and second parallel setup tasks including generation of beamformer tables and scan conversion tables, respectively; and instructing first and second CPUs to perform simultaneously said first and second parallel setup tasks, respectively.

15. The method of claim 1, further comprising:

re-dividing the signal processing operation into a new set of parallel signal processing tasks; and instructing the multiple CPUs to perform the new set of parallel signal processing tasks.

16. The method of claim 1, wherein said dividing and instructing steps are carried out by a symmetrical multiprocessing operating system.

17. The method of claim 1, further comprising:

configuring a personal computer to include said multiple CPUs; and operating a symmetrical multiprocessing operating system in the personal computer to carry out the dividing and instructing steps.

18. The method of claim 1, further comprising:

configuring a personal computer to include said multiple CPUs.

19. A method of processing ultrasound information in a medical diagnostic imaging ultrasound system having multiple CPUs configured to perform parallel ultrasound operations, said method comprising:

collecting data sets representative of patient ultrasound scans of an area of interest of a patient;

dividing a scan conversion operation into parallel scan conversion tasks;

instructing multiple CPUs to perform, in parallel, scan conversion tasks upon said data sets to form scan converted data sets, said multiple CPUs processing said scan conversion operations simultaneously and in parallel;

reassigning uncompleted scan conversion tasks among said multiple CPUs based upon completion of at least one of said scan conversion tasks; and presenting to a user ultrasound information related to said ultrasound scan based on said scan converted data sets.

20. The method of claim 19, further comprising:

dividing signal processing operations into parallel signal processing tasks; and instructing the multiple CPUs to perform, in parallel, signal processing tasks and scan conversion tasks upon data sets to form processed data sets.

21. The method of claim 19, further comprising:
instructing the multiple CPUs to perform parallel system control tasks simultaneously and in parallel with said parallel scan conversion tasks.

22. The method of claim 19, further comprising:
interrupting operation of at least one of the multiple CPUs while performing associated parallel scan conversion tasks; and
instructing an interrupted CPU to perform a user-interface operation, while uninterrupted CPUs continue to perform associated parallel scan conversion tasks.

23. The method of claim 19, further comprising:
determining when a first CPU completes an associated first parallel scan conversion task and at least a second CPU has not completed an associated second parallel scan conversion task; and
instructing the first CPU to complete the second parallel scan conversion task and the second CPU to cease performing the second parallel scan conversion task.

24. The method of claim 19, wherein said dividing step includes dividing a data set associated with a single image frame into data subsets based on a number of CPUs, wherein each data subset corresponds to a unique segment of the image frame and wherein said instructing step instructs each CPU to perform a parallel scan conversion task upon a corresponding data subset of a single image frame.

25. The method of claim 19, wherein the dividing step divides the data set into at least two data subsets corresponding to at least two unique quadrants of an ultrasound scan and having substantially similar complexity.

26. The method of claim 19, wherein the collecting step collects at least first and second data sets corresponding to first and second image frames of an area of interest, respectively; and the instructing step instructs first and second CPUs to perform all scan conversion upon corresponding first and second data sets, respectively.

27. The method of claim 19, wherein each parallel scan conversion task includes all scan conversion for a data set associated with an image frame of the area of interest.

28. The method of claim 19, wherein the instructing step assigns each CPU to a data set associated with a complete image frame of the area of interest, the multiple CPUs being assigned to successive image frames.

29. The method of claim 19, wherein the instructing step directs at least two CPUs to perform parallel scan conversion tasks upon at least two unique data subsets representing unique segments of a single ultrasound scan.

30. The method of claim 19, further comprising:
waiting until completion of said scan conversion operation by all of the multiple CPUs before beginning another ultrasound operation.

31. The method of claim 19, further comprising:
re-dividing the scan conversion operation into a new set of parallel scan conversion tasks; and
instructing the multiple CPUs to perform the new set of parallel scan conversion tasks.

32. The method of claim 19, wherein said dividing and instructing steps are carried out by a simultaneous multi-processing operating system.

33. The method of claim 19, further comprising:
configuring a personal computer to include said multiple CPUs; and
operating a simultaneous multiprocessing operating system in the personal computer to carry out the dividing and instructing steps.

34. The method of claim 19, further comprising:
configuring a personal computer to include said multiple CPUs.

35. An ultrasound apparatus for presenting medical diagnostic imaging ultrasound information to a user representative of an ultrasound scan of an area of interest, said apparatus comprising:
an input receiving data values representative of echo signals of patient ultrasound scans of an area of interest of a patient;
multiple CPUs configured to perform ultrasound operations in parallel upon data values received at said input;
operating modules for instructing said multiple CPUs to perform ultrasound operations upon said data values to produce ultrasound information, at least one of said operating modules dividing a corresponding ultrasound operation into a plurality of tasks, each of said multiple CPUs being assigned a unique task, said CPUs performing said tasks associated with a single ultrasound operation in parallel, at least one of said operating modules reassigning uncompleted tasks among said multiple CPUs based upon completion of at least one task from said plurality of tasks; and
an output for presenting said ultrasound information to a user.

36. The apparatus of claim 35, wherein said operating module includes a signal processing module that divides signal processing operations into signal processing tasks, each signal processing task operating upon a unique subset of data values, said CPUs processing said subsets of data values in parallel.

37. The apparatus of claim 35, wherein said operating module includes a scan conversion module that divides scan conversion operations into scan conversion tasks, each scan conversion task operating upon a unique subset of data values, said CPUs scan converting said subsets of data values in parallel.

38. The apparatus of claim 35, wherein said operating module instructs each CPU to perform all ultrasound tasks associated with a single image frame of an area of interest.

39. The apparatus of claim 35, wherein said operating module includes a beamformer module that divides beamforming operations into beamforming tasks, each beamforming task operating upon a unique subset of data values, said CPUs beamforming said subsets of data values in parallel.

40. The apparatus of claim 35, wherein said operating module includes a setup module that generates tables for use by said operating module s when performing ultrasound operations, said setup module dividing table generation into at least first and second tasks, a first CPU generating tables associated with a first task and a second CPU generating tables associated with a second task.

41. The apparatus of claim 35, wherein said operating modules includes signal processing and scan conversion modules that are divided into signal processing and scan conversion tasks, respectively, said multiple CPUs first performing said signal processing tasks in parallel and then performing said scan conversion tasks in parallel.

42. The apparatus of claim 35, further comprising:
a user-interface for accepting input from a user; and
a user-interface module interrupting operation of at least one of said multiple CPUs and instructing an interrupted CPU to perform a user-interface operation based on a user input, while uninterrupted CPUs continue to perform parallel tasks.

43. The apparatus of claim 35, wherein said operating module includes a 3-D rendering module that divides 3-D rendering operations in 3-D rendering tasks, each 3D rendering task operating upon a unique subset of data values.

44. The apparatus of claim 35, further comprising a probe receiving echo signals and a front end subsystem, said front end subsystem having a plurality of A/D converters to convert analog echo signals associated with each element of the probe into said digital values and having buffer memory for storing said data values, said front end subsystem passing the data values to a beamformer software module which instructs said multiple CPUs to perform beamforming operations upon the data values.

45. The apparatus of claim 35, further comprising a probe receiving echo signals.

46. The apparatus of claim 35, further comprising:

a simultaneous multiple processor operating system controlling said multiple CPUs in accordance with instructions from said operating modules.

47. The apparatus of claim 35, further comprising:

a personal computer including said multiple CPUs and including a simultaneous multiple processor operating system to control said multiple CPUs in accordance with instructions from said operating modules.

48. The apparatus of claim 35, further comprising:

a personal computer including said multiple CPUs.

* * * * *